US00PP30993P2

(12) United States Plant Patent
Hammett

(10) Patent No.: US PP30,993 P2
(45) Date of Patent: Oct. 29, 2019

(54) ***DAHLIA* PLANT NAMED 'MYSTIC WIZARD'**

(50) Latin Name: *Dahlia variabilis*
Varietal Denomination: Mystic Wizard

(71) Applicant: Keith Hammett, Auckland (NZ)

(72) Inventor: Keith Hammett, Auckland (NZ)

(73) Assignee: KiwiFlora Ltd., Auckland (NZ)

( * ) Notice: Subject to any disclaimer, the term of this patent is extended or adjusted under 35 U.S.C. 154(b) by 0 days.

(21) Appl. No.: 15/932,896

(22) Filed: May 17, 2018

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 6/144; A01H 5/02
See application file for complete search history.

*Primary Examiner* — Keith O. Robinson

(57) ABSTRACT

A new cultivar of *Dahlia* plant named 'Mystic Wizard' that is characterized by an upright and uniform growth habit, dark grey-green compound leaves, purple ray florets with involute cuspidate tips and red-purple disc florets with yellow styles and orange pollen.

1 Drawing Sheet

Botanical classification: *Dahlia variabilis.*
Variety denomination: 'Mystic Wizard'.

BACKGROUND OF THE INVENTION

The present invention relates to a new and distinct cultivar of *Dahlia* plant botanically known as *Dahlia variabilis* and hereinafter referred to by the cultivar name 'Mystic Wizard'.

The new cultivar is the product of a breeding program conducted by the inventor in a cultivated area of Auckland, New Zealand. The objective of the breeding program is to develop new *Dahlia* cultivars with unique flower and foliage colors.

'Mystic Wizard' originated from a cross of the female or seed parent *Dahlia variabilis* 'Home Run' (not patented) with mixed pollen from a number of *Dahlia variabilis* cultivars. The exact male or pollen parent is unknown. The crossing occurred in 2011 in Auckland, New Zealand. The resulting seeds were subsequently planted and grown. The cultivar 'Mystic Wizard' was selected in 2012 as a single plant within the stated progeny in a controlled environment of Auckland, New Zealand.

Asexual reproduction by terminal cuttings of the new cultivar 'Mystic Wizard' was first performed in 2012 in Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dahlia* cultivar 'Mystic Wizard'. These traits in combination distinguish 'Mystic Wizard' as a new and distinct cultivar apart from all other existing varieties of *Dahlia* known to the inventor.

1. *Dahlia* 'Mystic Wizard' exhibits an upright and uniform growth habit.
2. *Dahlia* 'Mystic Wizard' exhibits dark grey-green compound leaves.

3. *Dahlia* 'Mystic Wizard' exhibits purple ray florets with involute cuspidate tips.
4. *Dahlia* 'Mystic Wizard' exhibits red-purple disc florets with yellow styles and orange pollen.

The closest comparison varieties are the female or seed parent plant *Dahlia* 'Home Run', *Dahlia* 'Mystic Wonder' (U.S. Plant Pat. No. 24,397) and *Dahlia* 'Mystic Enchantment' (U.S. Plant Pat. No. 23,332). 'Mystic Wizard' is different than 'Home Run' in the following characteristics:

1. *Dahlia* 'Mystic Wizard' exhibits leaves that are darker grey-green in color than the leaves of 'Home Run'.
2. *Dahlia* 'Mystic Wizard' exhibits purple ray florets with involute cuspidate tips. In contrast, the ray florets of 'Home Run' are red-purple with an acute tip.
3. *Dahlia* 'Mystic Wizard' exhibits purple disc florets. In contrast, the disc florets of 'Home Run' are crimson.

'Mystic Wizard' is different than 'Mystic Wonder' in the following characteristics:

1. *Dahlia* 'Mystic Wizard' exhibits leaves that are lighter in color than the leaves of 'Mystic Wonder'. In contrast, the leaves of 'Mystic Wonder' are brown-black in color.
2. *Dahlia* 'Mystic Wizard' exhibits purple ray florets with involute cuspidate tips. In contrast, the ray florets of 'Mystic Wonder' are red with an acute tip.
3. *Dahlia* 'Mystic Wizard' exhibits red-purple disc florets with yellow styles and orange pollen. In contrast, the disc florets of 'Mystic Wonder' are orange-red in color with yellow pollen.

'Mystic Wizard' is different than 'Mystic Enchantment' in the following characteristics:

1. *Dahlia* 'Mystic Wizard' exhibits leaves that are lighter in color than the leaves of 'Mystic Enchantment'. In contrast, the leaves of 'Mystic Enchantment' are brown-black in color.
2. *Dahlia* 'Mystic Wizard' exhibits purple ray florets with involute cuspidate tips. In contrast, the ray florets of 'Mystic Enchantment' are red with a minute acute tip.

BRIEF DESCRIPTION OF THE DRAWING

The accompanying photograph illustrates the distinguishing traits of *Dahlia* 'Mystic Wizard'. The plant in the photograph shows an overall view of a 12 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Dahlia* cultivar named 'Mystic Wizard'. Data was collected in Auckland, New Zealand from 12 month old outdoor field grown plants. The time of year was autumn in the Southern Hemisphere. The temperature averaged 20° Centigrade during the day and 10° Centigrade at night. The light level was natural outdoor light. Color determinations are in accordance with The Royal Horticultural Society Colour Chart 2015 edition, except where general color terms of ordinary dictionary significance are used. The growing requirements are similar to the species.

'Mystic Wizard' has not been tested under all possible conditions and phenotypic differences may be observed with variations in environmental, climatic, and cultural conditions, however, without any variance in genotype.

Botanical classification: *Dahlia* 'Mystic Wizard'.

Use: Ornamental.

Parentage: 'Mystic Wizard' originated from a cross of the female or seed parent *Dahlia* 'Home Run' with mixed pollen from a number of *Dahlia* cultivars.

Vigor: Moderate.

Growth habit: Broad upright.

Plant shape: Inverted triangle with flowers on top.

Suitable container size: 16 cm. containers and larger.

Height: 100 cm. in height.

Width: 75 cm. in width.

Low temperature tolerance: 1° Centigrade.

High temperature tolerance: 28° Centigrade.

Propagation: Tissue culture and terminal cuttings.

Time to initiate roots (summer and winter): Approximately 14 days to produce roots on an initial cutting at 20° Centigrade.

Time to produce a rooted cutting or liner (summer and winter): Approximately 30 days.

Crop time: From a rooted cutting, approximately 18 to 20 weeks are required to produce a finished flowering plant.

Root system: Fine and fibrous with stolons and tubers.

Stem:

*Branching habit*.—Free branching.
*Average number of lateral branches*.—*Average* 8 to 12.
*Pinching*.—Not required.
*Lateral branch diameter*.—4 mm. in diameter.
*Lateral branch length*.—50 cm. in length.
*Lateral branch strength*.—Strong.
*Stem color*.—Varies between 200A to 200C.
*Pubescence*.—Absent.
*Internode length*.—16 cm. between nodes.
*Shape*.—Round.
*Surface*.—Smooth, slightly glossy.

Foliage:

*Leaf arrangement*.—Opposite.
*Compound or single*.—Compound.
*Quantity of leaves per lateral branch*.—6 to 8.
*Quantity of leaflets per leaf*.—3.
*Leaf length*.—15 to 17 cm. in length.
*Leaf width*.—12 to 14 cm. in width.
*Leaflet length*.—6 to 8 cm. in length.
*Leaflet width*.—9 to 10 cm. in width.
*Leaf shape*.—Ovate, deeply serrated.
*Leaf apex*.—Acuminate.
*Leaf base*.—Attenuate.
*Texture* (*both surfaces*).—Smooth.
*Pubescence*.—Upper surface absent, lower surface sparsely covered with short hairs.
*Leaf margin*.—Serrate.
*Vein pattern*.—Pinnate.
*Young leaf color* (*upper surface*).—N189A.
*Young leaf color* (*lower surface*).—148B.
*Mature leaf color* (*upper surface*).—N189A.
*Mature leaf color* (*lower surface*).—148B.
*Vein color* (*upper surface*).—79A.
*Vein color* (*lower surface*).—148A.
*Leaf attachment*.—Petiolate.
*Petiole dimensions*.—4.5 to 6.0 cm. in length and 4.2 to 4.25 mm. in width.
*Petiole color*.—187A.

Inflorescence:

*Inflorescence type*.—Terminal, single row of ray florets surrounding a central cluster of disk florets, flowers are held high above the foliage.
*Inflorescence aspect*.—Upward and outward.
*Quantity of flowers per lateral stem*.—3.
*Quantity of buds per lateral stem*.—3.
*Quantity of flowers and buds per plant*.—Approximately 28.
*Flowering season*.—Mid-summer to autumn.
*Rate of flower opening*.—5 days for ray florets to be fully expanded.
*Fragrance*.—None.
*Bud length*.—31 to 32 mm. in length.
*Bud diameter*.—18 to 19 mm. in diameter.
*Bud shape*.—Oblate.
*Bud color*.—200A and 200B.
*Inflorescence aspect*.—Outward-upright.
*Flower dimensions*.—11 to 12 cm. in diameter and 2.5 cm. in height.
*Flower longevity*.—Approximately 10 days.
*Ray floret number*.—8 to 10.
*Ray floret appearance* (*both sides*).—Matte.
*Ray floret texture* (*both sides*).—Smooth.
*Ray floret fused or unfused*.—Unfused.
*Ray floret shape*.—Obovate.
*Ray floret longitudinal axis*.—Straight.
*Ray floret margin*.—Entire.
*Ray floret apex*.—Involute cuspidate.
*Ray floret base*.—Attenuate.
*Ray floret dimensions*.—4.25 to 4.5 cm. in length and 2.5 to 2.75 cm. in width.
*Ray floret color when opening* (*upper side*).—N79 A to N79B.
*Ray floret color when opening* (*under side*).—N79 A to N79B.
*Ray floret color fully open* (*upper side*).—N79 A to N79B.
*Ray floret color fully open* (*under side*).—N79 A to N79B.
*Ray floret color fading*.—Not fading.
*Disc floret type*.—Daisy, collar segments absent.
*Disc floret number*.—70 per flower.
*Disc floret texture* (*both sides*).—Smooth.
*Disc floret shape*.—Tubular, corolla fused.
*Disc floret apex*.—Acute.

*Disc floret dimensions.*—12 mm. in length and 3 mm. in width.
*Disc floret color* (*upper side*).—59A.
*Disc floret color* (*under side*).—59A.
*Receptacle dimensions.*—8 mm. in depth and 2.5 cm. in diameter.
*Receptacle surface.*—Smooth.
*Self-cleaning or persistent.*—Self-cleaning.

Peduncle:
*Peduncle dimensions.*—15 to 23 cm. in length and 2.35 mm. in diameter.
*Peduncle angle.*—45° from vertical.
*Peduncle color.*—Varies between 200A and 200C.
*Peduncle strength.*—Moderately strong.

Reproduction organs:
*Stamen number.*—5 in number on disc florets only.
*Anther shape.*—Cylindrical, fused to tube wall.
*Anther dimensions.*—4.9 mm. in length and 0.6 mm in width.
*Anther color.*—59A.
*Amount of pollen.*—High.
*Pollen color.*—24B.
*Pistil number.*—One, on both ray and disc florets.
*Pistil length.*—Average 15 mm.
*Stigma shape.*—Bifid.
*Stigma color.*—59A.
*Style length.*—12 mm.
*Style color.*—3D.
*Ovary color.*—3D.

Fruit and seed:
*Fruit shape.*—Napiform capsule.
*Fruit dimensions.*—26 mm: in length and 19 mm. in width.
*Fruit color.*—N187A.
*Seed dimensions.*—12 mm. in length and 3.5 mm. in width.
*Seed color.*—203D.

Disease resistance: Plants of the new *Dahlia* have not been observed for disease resistance.

The invention claimed is:

1. A new and distinct variety of *Dahlia* plant named 'Mystic Wizard' as described and illustrated.

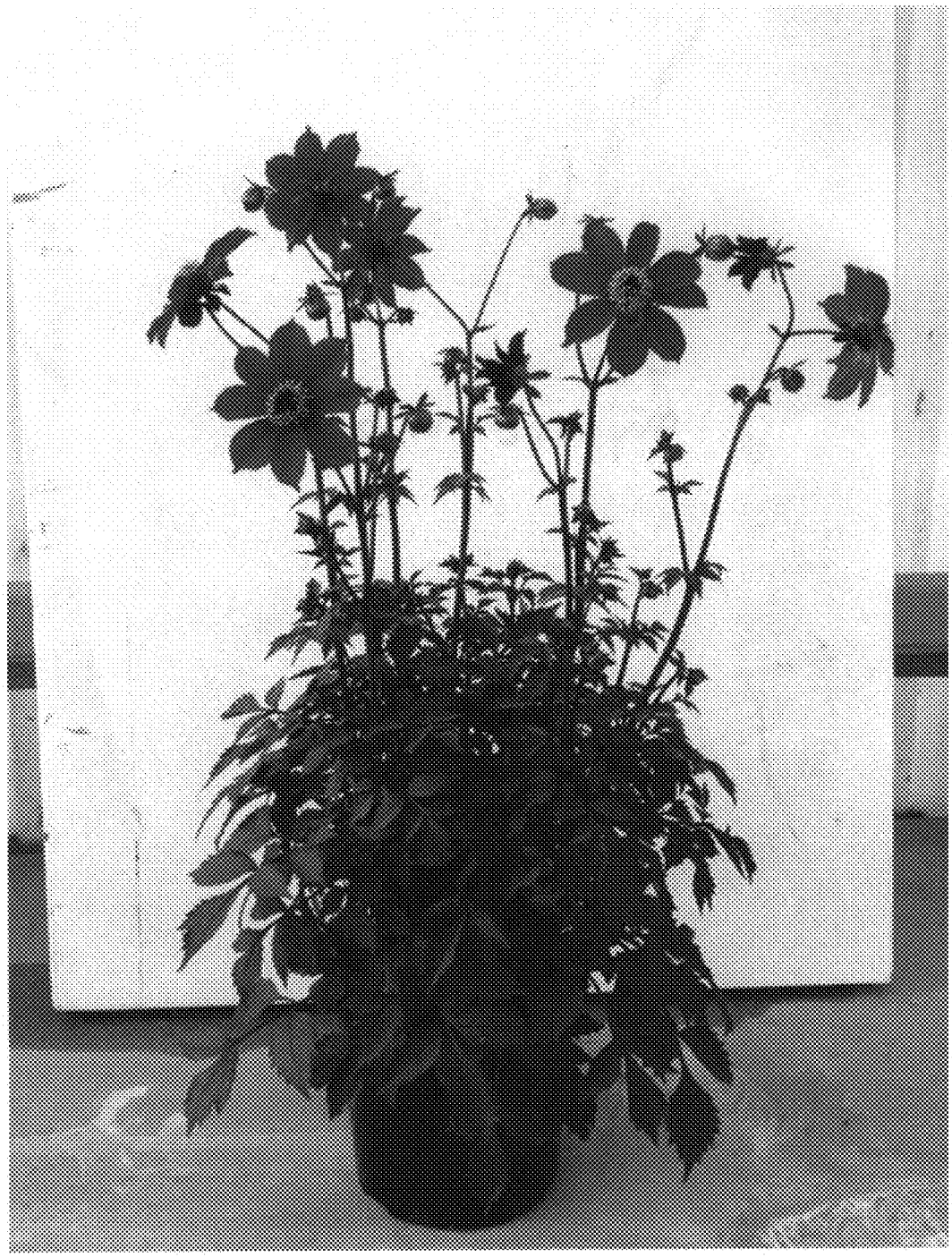

* * * * *